United States Patent [19]

Yu

[11] 4,046,781

[45] Sept. 6, 1977

[54] BIS-[5-(4-CHLOROPHENYL)FURFURYL]-DIALKYLAMMONIUM BROMIDES

[75] Inventor: Chia-Nien Yu, Norwich, N.Y.

[73] Assignee: Morton-Norwich Products, Inc., Norwich, N.Y.

[21] Appl. No.: 687,404

[22] Filed: May 17, 1976

[51] Int. Cl.$^2$ .......................................... C07D 307/52
[52] U.S. Cl. ................................. 260/347.7; 424/285
[58] Field of Search ...................................... 260/347.7

[56] References Cited

U.S. PATENT DOCUMENTS 3,277,118   10/1966   Schmid et al. .................... 260/347.7

OTHER PUBLICATIONS

Karrer, Organic Chemistry, New York – Elsevier Pub. Co. (1950) 4th Ed., p. 128.
Sommer et al., J. Org. Chem. (1971), vol. 36, No. 6, p. 824–828.

*Primary Examiner*—Henry R. Jiles
*Assistant Examiner*—Bernard Dentz
*Attorney, Agent, or Firm*—Anthony J. Franze

[57] ABSTRACT

This invention provides a series of bis-[5-(4-chlorophenyl)furfuryl]alkylammonium bromides having utility as antibacterial agents.

4 Claims, No Drawings

BIS-[5-(4-CHLOROPHENYL)FURFURYL]DIALKYLAMMONIUM BROMIDES

This invention is concerned with a series of bis-[5-(4-chlorophenyl) furfuryl]alkylammonium bromides of the formula:

wherein R and $R^1$ are methyl or n-butyl. These compounds are readily prepared by reacting 5-(4-chlorophenyl)furfuryl bromide with the appropriate secondary amine in the presence of an inert solvent such as benzene.

The compounds of this invention are effective antibacterial agents. In the commonly employed serial dilution method for assaying in vitro antibacterial potency they are capable of inhibiting the growth of microorganisms such as Staphylococcus aureus, Escherichia coli, Salmonella typhosa, Hemophilus vaginalis and Streptococcus agalactiae at concentrations of from 0.19 to 50 micrograms of compound per milliliter of test media. They are thus adapted to be combined in various formulations such as unguents, dusts, solutions, sprays and suspensions using conventional adjuvants and excipients as carriers therefor to eradicate and prevent bacterial growth.

In order that this invention may be readily understood by and available to those skilled in the art, the following examples of the compounds thereof are appended.

EXAMPLE I bis-[5-(p-Chlorophenyl)furfuryl]dimethylammonium Bromide

A. A solution of 37.5 g (0.148 g) of phosphorus tribromide in 300 ml of anhydrous ether was added dropwise in about 1 ½ hr to a solution of 78.3 g (0.375 m) of 5-(p-chlorophenyl)furfuryl alcohol in 800 ml of anhydrous ether at 0°-5°. The dark reaction mixture was allowed to stir for an additional 1 hr after addition was completed. The ethereal solution was decanted from the gummy material. The gummy material was further extracted with 2 × 150 ml of ether. The ethereal extracts were combined, washed with 3 × 150 ml of 20% sodium hydroxide solution and then with 3 × 150 ml of water. After drying over MgSO₄, ether was evaporated off at reduced pressure to give a beige colored solid. The solid was dissolved in 600 ml of benzene.

B. A suspension of 161 g (2 m) of dimethylamine hydrochloride and 110 g (0.8 m) of anhydrous potassium carbonate in 1200 ml of benzene was stirred at room temperature for 1 hr. The mixture was then warmed on a steam bath for about 5-10 min. The above benzene solution (600 ml) of the furfuryl bromide was then added dropwise to this suspension. The temperature of the reaction mixture was maintained around 50°-60° with occasional warming during the addition (1 ½ hr). The reaction mixture was allowed to stir further at ambient temperature for 2 hr after the addition. After standing overnight the reaction mixture was filtered and the solid was washed with benzene and air-dried. The solid was then triturated well with water, filtered, washed well with water and dried at 100° to give 18 g (9.5%) of title compound; m.p. 194°-195°.

Anal. Calcd. for $C_{24}H_{22}Cl_2NO_2{}^+Br^-$: C, 56.82%; H, 4.37%; N, 2.76%; Found: C, 57.10%; H, 4.36%; N, 2.71%

EXAMPLE II

Bis-[5-(4-chlorophenyl)furfuryl]-n-butylmethylammonium Bromide

To a solution of 5-(4-chlorophenyl)furfuryl alcohol (52.2 g, 9.25 ml) in 550 ml of anhydrous ether was added in about 30 min a solution of 25 g (0.098 m) of phosphorus tribromide in 200 ml of anhydrous ether. The temperature of the reaction was kept at 0°-5° during the addition. The reaction mixture was allowed to stir for another 1 ½ hr. The top ethereal solution was decanted from the gummy material at the bottom of the flask. The gummy material was further extracted with 2 × 200 ml of ether. The ethereal extracts were combined, washed with 3 × 150 ml of 20% NaOH solution, followed by 4 × 150 ml of water. After drying over MgSO₄, ether was evaporated off at reduced pressure to give a beige colored solid. The yield of the furfuryl bromide was 64 g (94%).

The above bromide was dissolved in 1 l. of benzene and 10.3 g (0.125 m) of n-butylmethylamine was added with stirring. The temperature of the reaction mixture went up from 22° to 28° and in about one-half hr solid started to separate. The mixture was allowed to stir further overnight and then filtered. The solid was washed with benzene and air-dried. The yield of title compound was 26.5 g (39%), m.p. 174°-176°.

Anal. Calcd for $C_{27}H_{28}BrCL_2NO_2$: C, 59.03%; H, 5.14%; N, 2.55%; Found: C, 58.89%; H, 5.24%; N, 2.54%

EXAMPLE III

Bis[5-[4-chlorophenyl]furfuryl]di-n-butylammonium Bromide

To a benzene solution (500 ml) of 5-(4-chlorophenyl)-2-furfuryl bromide under stirring at room temperature was added 11.7 g (0.09 ml) of di-n-butylamine. Solid started to separate after 3 hr of stirring, and the mixture was filtered after overnight stirring. The solid was washed with benzene, ether and air-dried. Recrystallization of the crude waxy solid from 75 ml of acetonitrile gave 3.1 g (5.9%) of title compound.

Anal. Calcd for $C_{30}H_{34}BrCL_2NO_2$: C, 60.92%; H, 5.79%; N, 2.37%; Found: C, 60.89%; H, 5.67%; N, 2.33%

What is claimed is:

1. A compound of the formula:

wherein R and $R_1$ are methyl or n-butyl.

2. The compound bis-[5-(4-chlorophenyl)furfuryl]-dimethylammonium bromide.

3. The compound bis-[5-(4chlorophenyl)furfuryl]n-butylmethylammonium bromide.

4. The compound bis-[5-(4-chlorophenyl)furfuryl]di-n-butylammonium bromide.